United States Patent [19]

Drake et al.

[11] Patent Number: 4,654,461

[45] Date of Patent: Mar. 31, 1987

[54] PRODUCTION OF HIGH (Z,Z) CONTENT 1,5,9-TETRADECATRIENE

[75] Inventors: Charles A. Drake; M. Bruce Welch, both of Bartlesville, Okla.

[73] Assignee: Phillips Petroleum Company, Bartlesville, Okla.

[21] Appl. No.: 851,987

[22] Filed: Apr. 14, 1986

[51] Int. Cl.[4] .......................... C07C 2/02; C07C 11/21
[52] U.S. Cl. ..................................... 585/600; 585/646
[58] Field of Search ................................ 585/600, 646

[56] References Cited

U.S. PATENT DOCUMENTS

| | | | |
|---|---|---|---|
| 3,365,513 | 1/1968 | Heckelsberg | 585/643 |
| 3,586,731 | 6/1971 | Heckelsberg | 585/643 |
| 3,637,893 | 1/1972 | Singleton | 585/600 |
| 3,658,927 | 4/1972 | Crain et al. | 585/367 |
| 3,715,410 | 2/1973 | Ray et al. | 585/600 |
| 3,739,037 | 6/1973 | Cywinski | 585/375 |
| 4,331,814 | 5/1982 | Chabardés et al. | 585/600 |

*Primary Examiner*—Asok Pal
*Attorney, Agent, or Firm*—Stephen E. Reiter

[57] ABSTRACT

Method for the production of high cis content 1,5,9-tetradecatriene is provided which comprises disproportionating 1,5-cyclooctadiene and 1-hexene in the presence of a catalyst consisting essentially of molybdenum oxide on a high purity, high surface area, high pore volume silica support. The resulting high cis content 1,5,9-tetradecatriene is a useful precursor for the preparation of gossyplure, a known insect sex attractant.

9 Claims, No Drawings

PRODUCTION OF HIGH (Z,Z) CONTENT 1,5,9-TETRADECATRIENE

This invention relates to the disproportionation of 1,5-cyclooctadiene and 1-hexene. In one aspect, this invention relates to the production of high (Z,Z) content 1,5,9-tetradecatriene by disproportionation. In another aspect, this invention relates to chemical intermediates useful for the production of products having insect sex attractant properties.

BACKGROUND

Gossyplure, a 60/40 mixture of Z,Z and Z,E stereoisomers of 7,11-hexadecadienyl acetate, is a known pheromone for several insect species. In order to make this compound widely available for use in insect control, economic large scale synthetic conversion processes must be developed. One of the most promising synthetic conversion processes developed to date is the process whereby 1,5,9-tetradecatriene is metallated to produce a 1-metallo-5,9-tetradecadiene, which compound is then homologized by addition of a $C_2$-synthon, then esterified as needed to produce the desired gossyplure-like product.

A key to the success of the above-described synthetic route is the availability of a triene starting material with a stereochemical content that approaches as closely as possible the 60/40 Z,Z to Z,E ratio for the internal double bonds of the triene, as observed in naturally occurring gossyplure.

OBJECTS OF THE INVENTION

An object of the present invention, therefore, is a method for the production of 1,5,9-tetradecatriene which has a high 5Z,9Z to 5Z,9E ratio.

Another object of the present invention is to provide 1,5,9-tetradecatriene composition of matter which comprise at least fifty percent cis (or Z) content at the 9-carbon, and essentially 100 percent cis content at the 5-carbon.

These and other objects of the invention will become apparent from further study of the disclosure and claims herein provided.

STATEMENT OF THE INVENTION

In accordance with the present invention, we have discovered that 1,5,9-tetradecatriene having a high cis content at the 9-carbon and essentially all cis content at 5-carbon is obtained when 1,5-cyclooctadiene and 1-hexene are contacted under disproportionation conditions in the presence of a catalyst consisting essentially of molybdenum oxide on a high purity, high surface area, high pore volume silica support.

DETAILED DESCRIPTION OF THE INVENTION

In accordance with the present invention, a method for the preparation of 1,5,9-tetradecatriene having a cis content at the 9-carbon in excess of fifty percent and an essentially all cis orientation at the 5-carbon is provided which comprises contacting 1,5-cyclooctadiene and 1-hexene under disproportionation conditions in the presence of a catalyst consisting essentially of molybdenum oxide on a high purity, high surface area, high pore volume silica support.

In accordance with one embodiment of the present invention, there is provided as a composition of matter 1,5,9-tetradecatriene which has a cis content at the 9-carbon of at least fifty percent, and an essentially all cis orientation at the 5-carbon.

The disproportionation catalyst useful in the practice of the present invention is prepared from a high purity, high surface area, high pore volume silica support. For purpose of this disclosure, high purity means an essentially dry support containing at least about 99 percent silica by weight, preferably containing at least about 99.6 percent silica by weight and no greater than about 0.2 weight percent alumina; the phrase "high surface area" refers to silicas having surface areas of at least 200 meters squared per gram ($m^2/g$), preferably having surface areas of 250 $m^2/g$ and higher; and the phrase "high pore volume" refers to silicas have pore volumes of at least 0.6 cubic centimeters per gram ($cm^3/g$), preferably having pore volumes of 1.0 $cm^3/g$ and higher. Those of skill in the art recognize that, in general, the higher the surface area, the lower the pore volume of a given support material will be, and vice versa. Thus, silica supports having substantially higher surface areas than those specified herein will not be able to simultaneously achieve the desired high pore volumes; and conversely, silica supports having substantially higher pore volumes than those specified herein will not be able to simultaneously achieve the desired high surface areas. Therefore, the required minimum values set forth herein for surface area and pore volume indirectly place an upper limit as to how high these values may go.

The support is contacted with molybdenum oxide or a precursor thereof, such as for example, ammonium molybdate and optionally, additional support treating reagents such as alkali metal hydroxides, e.g., potassium hydroxide, sodium hydroxide, and the like. Support-treating agent contacting is carried out in any suitable manner. For example, the silica and molybdenum oxide or mulybdenum oxide precursor can be mixed in an open vessel. When the molybdenum oxide or molybdenum oxide precursor is provided as a solution, such as for example, an aqueous solution, once the silica support and support treating solution are mixed, then any excess liquid can be decanted or removed by filtration. Alternatively, the technique of incipient wetness can be employed whereby only enough liquid is employed to thoroughly wet the silica support, with no free residual liquid. Thus, only as much support-treating solution is employed as the silica support can absorb. This can be accomplished, for example, by spraying support-treating solution over a quantity of silica which is being tumbled in a rotating, baffled drum. Such treatment can also be carried out by simply pouring a predetermined quantity of support-treating solution over a quantity of silica support contained in an open vessel. Alternatively, a measured quantity of silica support could be added to a volume of support-treating solution such that all the liquid is imbibed by the added support. Other techniques as are known to those skilled in the art can also be employed. For example, a quantity of silica support may be placed in a tubular reactor, a volume of support-treating solution may be percolated therethrough, followed by further treatment/activation as necessary.

The conditions of silica support/support-treating reagent contact are not critical. Any temperature and any period of contact time is generally suitable. For convenience, contacting is generally carried out at about room temperature, although both higher or lower temperatures can be employed. When support-treating reagents are provided as an aqueous solution, contacting is preferably carried out at a temperature not exceeding about 100° C. A time period sufficient to allow the support and reagents to come into intimate contact is all that is necessary. Thus, the silica support and support-treating reagents may be brought into contact for as little time as a few seconds to several hours or more, as convenient.

Following contact of the silica support and support-treating reagents, any excess liquid (if solvent or diluent is employed) can be removed by suitable means, such as, for example, decantation, filtration, or the like. The treated support can then be dried to remove absorbed solvent. Any suitable means, as well known by those skilled in the art, may be employed, such as for example, over drying, azeotropic removal of solvent, passing a vigorous stream of dry (i.e., moisture-free) gas over the treated support, and the like. For example, the treated support can be dried by heating at an elevated temperature of about 200° C. or higher by passage of an inert gas such as nitrogen over the treated support. This can be accomplished within the reactor or in other suitable catalyst preparation equipment.

Calcination, when used, in conducted by heating the treated catalyst in the presence of an oxygen-containing gas, such as for example, air, under conditions sufficient to activate the molybdenum oxide or to convert the molybdenum compound present to the active oxide form. Temperatures in the range of about 300° C. up to about 800° C. are generally satisfactory for such calcination. The time for subjecting the treated silica support to calcination is an amount of time sufficient to activate the treated support. Anywhere from a few minutes to several hours is suitable. Typically, about 15 minutes up to about 20 hours of calcination will be sufficient. Preferably, for most efficient use of reaction equipment, calcination will be carried out for in the range of about 30 minutes up to 6 hours. Typically, less time is required at higher temperatures and vice versa. After calcination, the activated catalyst can optionally be treated under reducing conditions, such as for example, with carbon monoxide, hydrogen, or a hydrocarbon, at a temperature in the range of about 400° up to about 750° C. in order to enhance the disproportionation activity of the catalyst. Such reducing treatment is carried out preferably at temperatures in the range of about 500° up to about 650° C., because good catalyst activity with reasonably short activation periods of about 1 up to about 6 hours is ahieved. Such optional reducing treatment can suitably be carried out for a period of time ranging from about 1 minute up to about 30 hours. If desired, the thus calcined disproportionation catalyst can further by treated with an inert gas such as nitrogen prior to use in a conversion process in order to remove materials from the catalyst which may have a detrimental effect on subsequent disproportionation reactions.

The proportion of molybdenum oxide or oxide precursor combined with the silica support can vary appreciably, but generally the support will contain at least about 0.1 percent by weight of the metal, calculated as the oxide and based on the combined weight of metal oxide and inorganic oxide support. Generally, the support will contain an upper limit of about 40 percent by weight of molybdenum, calculated as the oxide and based on the combined weight of metal oxide and silica support. Amounts of about 0.2 up to 40 percent by weight of the metal, calculated as the oxide, are preferred, with amounts in the range of about 2 up to 20 percent by weight of the metal, calculated as the oxide, being especially preferred because good catalyst reactivities and product selectivities are obtained within this concentration range. Optional treating reagents such as potassium hydroxide and the like can be added in amounts ranging from 0.1 up to about 5 percent by weight of metal, calculated as the oxide and based on the combined weight of silica support and the total weight of treating reagents.

Typically the disproportionation reaction is carried out at a temperature in the range of about 0° up to 400° C.; preferably for good conversion in relatively short reaction times, temperatures in the range of about 50° up to 250° C. are employed.

The disproportionation reaction can be carried out by contacting the olefins to be disproportionated with the catalyst in the liquid phase or the gas phase. Pressure during the disproportionation reaction can vary between wide limits. For example, pressures between about 0.1 and 500 atmospheres are suitable, although pressures in the range of about 1 up to 40 atmospheres are preferred because good conversions are obtained with readily available reaction equipment.

If the reaction is carried out in the liquid phase, solvents or diluents for the reactants can be used. Aliphatic saturated hydrocarbons, e.g., pentanes, hexanes, cyclohexanes, dodecanes, and aromatic hydrocarbons, such as benzene and toluene are suitable. If the reaction is carried out in the gaseous phase, diluents such as saturated aliphatic hydrocarbons, for example, methane, ethane, and/or substantially inert gases, e.g., nitrogen or argon, can be present. Preferably, for high product yield, the disproportionation reaction is effected in the absence of significant amounts of deactivating materials such as water and oxygen.

The olefin reactants, 1,5-cyclooctadiene and 1-hexene, can be contacted in any ratio. For efficient use of starting materials, the molar ratio of 1,5-cyclooctadiene to 1-hexene will generally vary within the range of 5:1 up to 1:5, with ratios in the range of about 2:1 up to 1:2 preferred.

The contact time needed to obtain a reasonable yield of disproportionation products depends upon several factors, such as for example, the metals loading on the catalyst, reactor dimensions, temperature, pressure, and the like. The length of time during which the olefinic reactants to be disproportionated are contacted with the catalyst can conveniently vary between 0.1 seconds and 24 hours, although longer and shorter contact times can be used. Preferably, for efficient use of reactor equipment, times in the range of about 1 second up to 1 hours are used. This can alternatively be expressed in terms of liquid hourly space velocity (LHSV) which can vary in the range of 0.1 up to 100.

The process of the present invention can be carried out batch wise or continuously employing fixed catalyst beds, slurried catalyst, fluidized beds, or by using any other conventional contacting techniques.

A further understanding of the present invention and its advantages will be provided by reference to the following non-limiting examples.

EXAMPLE I

Catalyst Preparation

Several different silica supports were impregnated with about 1.2 grams of ammonium molybdate by contacting about 10 grams of support with about 12 milliliters of water in which the ammonium molybdate was dissolved. Once intimate contact between the support and support-treating solution had been achieved, the treated silica was dried in a forced air oven at about 120° C. for about 3 hours, then calcined at about 350° C. for about three hours in a steady flow of air, resulting in a catalyst containing about 10 weight percent molybdenum oxide, calculated as the oxide and based on the total weight of support and oxide. The designations given the resulting catalysts and some physical and chemical properties of the different supports used are summarized in Table I.

TABLE I

| Catalyst | Silica Source | Pore Volume, cm$^3$/g | Surface Area, m$^2$/g | Impurities, wt. % | |
|---|---|---|---|---|---|
| | | | | Na$_2$O | Al$_2$O$_3$ |
| A | Philadelphia Quartz CD 106 | 0.4 | 690 | <0.1 | 0.05 |
| B | Ketjen Si-2/5P | 1.05 | 250 | 0.07 | 0.3 |
| C | Air Products 29C2 | 1.2 | 316 | 0.3 | 0.4 |
| D | Davison G57 | 1.1 | 340 | 0.06 | 0.1 |

EXAMPLE II

Disproportionation Reactions

All runs were made by passing a mixture of 1,5-cyclooctadiene and 1-hexene downflow through a vertical pipe reactor (½ inch diameter and 20 inches in length) positioned in a temperature-controlled electric furnace. A thermocouple was positioned in the catalyst bed to monitor reaction temperature.

About 6 inches depth of quartz chips (minus 9 plus 12 mesh) were placed at the bottom of the pipe reactor supported by a layer of quartz wool. Another layer of quartz wool was placed on top of the quartz chips as support for a combined catalyst bed comprising about 1.5 grams of silica supported molybdenum oxide catalyst mixed with about 5 grams of α-alumina as an inert catalyst diluent. This was topped with another layer of quartz wool and the remainder of the reactor filled with quartz chips. The catalyst bed was activated by heating at 538° C. in flowing air for three hours, followed by about 15 minute treatment with flowing carbon monoxide at the same temperature, and finally the catalyst was cooled under flowing nitrogen to the desired reaction temperatures of about 200° C.

The olefinic reactants were first percolated through a 13X molecular sieve drier, then alumina and finally magnesium oxide prior to use. A cyclooctadiene/hexene feed ratio of about 40/60 was used for all runs.

All runs were carried out at a reaction temperature of about 200° C. and at a reaction pressure of about 200 psig. The mixed cyclooctadiene/hexene feed was introducted at a rate of about 4 mL/min., or at a weight hourly space velocity (WHSV) of about 120 grams of feed/gram of catalyst/hour.

The hot reactor effluent was vented to a hood; periodically the total effluent was sampled for analysis on a gas liquid chromatograph (GLC) by collection in a bomb held in dry ice. Analyses were carried out by injecting a portion of the chilled effluent on a 25 meter cyanopropyl silicone capillary column operated at 110° C. isothermal. Reaction results are summarized in Table II.

TABLE II

| Run | Catalyst | 1,5,9-TDT* Yield, % | Ratio |
|---|---|---|---|
| 1 | A | 4 | 47/53 |
| 2 | B | 4 | 45/55 |
| 3 | C | 5 | 47/53 |
| 4 | D | 9 | 54/46 |

*TDT is tetradecatriene

Only invention catalyst D, which has both high surface area, high pore volume and very low levels of impurities, especially low levels of alumina, gives a Z,Z to Z,E ratio in excess of 1:1, i.e., only invention catalyst D gives a triene product with greater than 50 percent cis content at the 9-carbon. In addition, invention catalyst D gives substantially higher yields of triene than do the comparison catalysts.

The examples have been provided merely to illustrate the practice of our invention and should not be read so as to limit the scope of our invention or the appended claims in any way. Reasonable variations and modifications, not departing from the essence and spirit of our invention, are contemplated to be within the scope of patent protection desired and sought.

We claim:

1. A method for producing 1,5,9-tetradecatriene having a cis content at the 9-carbon of at least 50%, and an essentially all cis orientation at the 5-carbon which comprises contacting 1,5-cyclooctadiene and 1-hexene under disproportionation conditions in the presence of a catalyst consisting essentially of molybdenum oxide on a high purity, high surface area, high pore volume silica support.

2. A method in accordance with claim 1 wherein said disproportionation conditions comprise a temperature in the range of 0° up to 400° C., a pressure in the range of 0.1 up to 500 atm, and a LHSV in the range of 0.1 up to 100.

3. A method in accordance with claim 1 wherein said silica support has a surface area of at least 200 m$^2$/g and a pore volume of at least 0.6 cm$^3$/g.

4. A method in accordance with claim 1 wherein said silica support contains no greater than 0.2 wt % Al$_2$O$_3$.

5. A method in accordance with claim 1 wherein said silica support is at least 99 percent silica by weight.

6. A method in accordance with claim 1 wherein said catalyst consists essentially of 0.2 up to 40 weight percent MoO$_3$ on the silica support, calculated as the oxide and based on the combined weight of oxide and support.

7. A method in accordance with claim 1 wherein said 1,5-cyclooctadiene and 1-hexene are contacted in a molar ratio in the range of about 5:1 up to 1:5.

8. As a composition of matter 1,5,9-tetradecatriene having a cis content at the 9-carbon of at least 50%, and an essentially all cis orientation at the 5-carbon.

9. A composition of matter in accordance with claim 8 wherein the cis content at the 9-carbon is within the range of about 50–60%.

* * * * *